(12) United States Patent
Farooqi et al.

(10) Patent No.: US 6,264,926 B1
(45) Date of Patent: Jul. 24, 2001

(54) FORMULATION USEFUL AS A NATURAL HERBAL TOOTH POWDER

(75) Inventors: Alaul Hasan Abad Farooqi; Srikant Sharma; Asifudulla Khan; Raghubind Kumar; Sushil Kumar, all of U.P. (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/268,334

(22) Filed: Mar. 16, 1999

(30) Foreign Application Priority Data

Feb. 12, 1999 (IN) .............................. 240/Del/1999

(51) Int. Cl.⁷ .............................. A61K 7/26; A61K 35/78
(52) U.S. Cl. .......................... 424/58; 424/195.1; 424/49
(58) Field of Search .................... 424/98, 195.1, 424/58

(56) References Cited

PUBLICATIONS

Almas et al., World Health Forum, 16:206–210 (1995).
Chopra et al., Glossary of Indian Medicinal Plants (1956).
Manandhar, J. Econ. Tax. Bot., 12:408–413 (1997).
Rao et al., Ethnobot, 8:88–91 (1996).
Rispler–Chaim V, J. Royal Asiatic Soc., V2:13–20 (1992) (abstract).
Sushil Kumar et al., Medicinal Plants in Skin Care, CIMAP, 76–89 (1994).
Farooqi et al., J. Med. Arom. Pl. Sci, 20:411–450 (1998).
Wealth of India, vol. 6, p. 90 (1994).
Wealth of India, vol. 8, pp. 351–352 (1994).
Wealth of India, vol. 9, p. 218 (1994).

*Primary Examiner*—Shep K. Rose
(74) *Attorney, Agent, or Firm*—Birch, Stewart, Kolasch & Birch, LLP

(57) ABSTRACT

The present invention relates to a formulation of herbal toothpowder or toothpaste for gums and teeth, which comprises of powder or paste of *Zanthoxylum armatum* (20–25%), *Zingiber officinale* (25–30%), *Santalum album* (8.25–8.5%), *Spilanthes calva* (2.0–2.5%), *Pistacia lentiseus* (2.0–2.5%), *Quercus infectoria* (8.0–8.5%), *Usnea longissima* (1–4%), as well as roasted alum and common salt.

8 Claims, No Drawings

FORMULATION USEFUL AS A NATURAL HERBAL TOOTH POWDER

FIELD OF INVENTION

This invention relates to the development of a formulation useful as a herbal tooth powder for gums and teeth. More particularly, the invention provides a formulation useful for the treatment of pyorrhoea, yellowing/staining of teeth and sensitivity of teeth to hot/cold water and food.

BACKGROUND OF INVENTION

The main diseases of the teeth include plaque, caries and pyorrhoea. Proper dental care is necessary for eliminating tooth decay and periodental diseases. The people living in Indian subcontinent largely depend on the traditional systems for the treatment of toothache, caries and other diseases related to teeth. The traditional herbal preparations for dental care comprise of various types of herbal powders and chewing sticks made out of young woody stem or root pieces. The table-1 gives a list of plants which are used for oral health by the people of India. It is compiled from the literature reports (Almass K., Al-Lafi, Tr., World Health Forum 16:206–210, 1995; Chopra et al., Glossary of Indian Medicinal Plants, 1956; Manandhar N P, J. Econ. Tax. Bot., 12:408–413, 1997; Rao et al. Ethnobot., 8:88–91, 1996; Rispler-Chaim V, J Royl Asiatic Soc. V2:13–20, 1992 and Sushil Kumar et al. Medicinal Plants in Skin Care, CIMAP, 76–89, 1994).

TABLE 1

The plants that are employed for tooth care in India

| Sl. No. | Botanical and Indian common names | Purpose and method of use |
|---|---|---|
| 1. | *Acacia catechu* (Katha) | Catechu paste is used to treat the bleeding gums and for tooth hypersensitivity. |
| 2. | *A. nilotica* (Kikar) | Fresh twig is used as tooth brush for keeping the gums and teeth healthy and clean. |
| 3. | *Achyrathes aspera* (Puthkanda, Latjira) | Twing is used for brushing teeth. to treat dental problems |
| 4. | *Azadirachta indica* (Neem) | Fresh twig is used as tooth brush to prevent gum diseases and pyorrhoea |
| 5. | *Aristolochia bracteolata* (Kidamari) | Root juice is applied to the site of toothache for relieving pain |
| 6. | *Cinnamomum camphora* (Kapur) | Tender twigs are chewed or the paste of stem bark is applied in aching teeth |
| 7. | *Cinnamomum verum* (Dalchini) | Powdered stem bark is applied to teeth in the treatment of caries and pyorrhoea |
| 8. | *Curcuma longa* (Turmeric) | Powder of rhizome is used in tooth powder for curing pyorrhoea |
| 9. | *Eucalyptus globulus* (Karpoora) | To prevent tooth decay and to provide relief form pain the leaf oil is applied to the site of pain |
| 10. | *Ficus bengalensis* (Bargad) | Aerial root is used as tooth brush and the latex is applied in toothache |
| 11. | *Juglans regia* (Akhrot) | Stem bark is used in tooth powders to make the teeth healthy |
| 12. | *Madhuca longifolia* (Mahua) | Stem bark is used in tooth powder for gum pain and toothache |
| 13. | *Mimusops elengi* (Maulsari) | Bark is used in tooth powder for the protection of gums and teeth |
| 14. | *Myristica fragrans* (Jaiphal) | Fruit paste is applied on teeth to cure dental caries and pyorrhoea |
| 15. | *Ocimum sanctum* (Tulsi) | Leaves are chewed as such for the treatment of bad breath and leaf paste is usefull for tooth hypersensitivity |
| 16. | *Piper betel* (Pan) | Leaf paste is suggested for dentinal hypersensitivity |
| 17. | *Piper longum* (Piplamus) | Fruit in the form of powder is applied for dental caries |
| 18. | *Piper nigrum* (Goal mirch) | Fine powder of seeds is applied to teeth in toothache, pyorrhoea and gum bleeding |
| 19. | *Potentilla fulgens* (Vajardanti) | Root powder is applied in gingivitis |
| 20. | *Punica granatum* (Anar) | Stem bark or fruits rind is used as component of dental powder |
| 21. | *Salvadora persica* (Pilu) | Twig is used as tooth brush for cleaning the teeth. Roots are used in dental caries, |

TABLE 1-continued

The plants that are employed for tooth care in India

| Sl. No. | Botanical and Indian common names | Purpose and method of use |
|---|---|---|
| | | and to relieve toothache |
| 22. | *Syzygium aromaticum* (Laung) | Clove oil is applied for toothache, dental caries and pyorrhoea |
| 23. | *Spilanthes calva* (Akarkara) | Flowers chewed in toothache. Plant made into paste is applied in toothache |
| 24. | Zanthoxylum armatum (Tejbal) | Twig is used as tooth brush for cleaning the teeth. Fruit powder is applied to teeth in toothache. |

In the Indian subcontinent the commonest source of chewing sticks is *Azadirachta indica*. *Salvador persica* stems and roots are also widely used as chewing sticks. Chewing sticks obtained from *A. indica* contain essential oils and exert carminative, antiseptic and analgesic action. The tannins of chewing sticks have an astringent effect on mucous membrane.

Many plants are useful in pyorrhoea. *Cinnamomum verum* bark is an astringent and is thus useful for checking the bleeding of gums. The bark has essential oil and tannins. The essential oil of *C. verum* has antimicrobial and antibacterial properties. *Accacia nilotica* bark and ash of almond kernel can be pulverized together and mixed with common salt to make a highly effective preparation to contain pyorrhoea and for strengthening of gums by making them strong. Use of clove oil is recommended for the alleviation of toothache.

At present, a number of tooth powders are available in India which contain cheap pulverized items that are not very effective as well as harmful for gums and teeth and have toxic effects. Composition of some of the herbal tooth powder available in market are given below.

| S.No. | Product name | Manufacturer and address | Ingredients |
|---|---|---|---|
| 1. | Red Tooth Powder | Dabur India Ltd. 22, Site IV Sahibabd, Ghaziabad | Pudina satva (Mentha sp.), lavang ka tail (*Syzygium aromaticum*), Tomer beej (*Zanthoxylum acanthopodium*), Kapoor, Kalimarich (*Piper nigrum*), Pippali (*Piper longum*), Sunthi (*Zingiber officinale*), Tambaku (*Nicotiana tabacum*) |
| 2. | Vicco Vajradanti | Vicco Laboratories 25, Jerbi Wadia Road, Parel, Bombay-400012 | Babbul (*Acacia nilotica*), Janibhul, Lavang (*Syzygium aromaticum*), Manjishtha (*Rubia cordifolia*), Dalchini (*Cinnamomum zeylanicum*), Vajradanti (*Potentilla fulgens*), Acrod, Khair patang, Akkal Kadha, Babul, Jeshthamadh, Kabachini (*Piper cubaba*), Anant root (*Hemidesmus indicus*), Ajwain (*Trachyspernum ammi*), Jaifal (*Myristica fragrans*), Trifala (*Emblica officinals, Terminalia chabula, Terminalia belerica*), rice husk, sugar, alum, salt. |
| 3. | Lordent Toothpowder | Lord's Cosmetics International A-21/27, Naraina Industrial Area, Phase-II New Delhi-110028 | Extract of Plantago, Calendula and creosote |
| 4. | Meghdoot dantusha | Meghdoot Gramodhyog Seva Sansthan, Meghdoot Buliding Chandganj Garden, Lucknow | Sonth (*Zingiber officinale*), Pipal (*Ficus religiosa*), Kalimirch (*Piper nigrum*), Tomar beej (*Zanthoxylum acanthopodium*), Samundar Jhag, Akarkara (*Anacyclus pyrethrum*) Manjuphal, |

-continued

| S.No. | Product name | Manufacturer and address | Ingredients |
|---|---|---|---|
| 5. | Payorin | Dawakhana Tibbiya College, AMU, Alighrh | Maulshri (*Mimosops elengi*), Sengdha salt. Amla (*Emblica officinalis*) Sokhta, Gile gaimuliya, Taj galmi, Kafoor khlis, Hamize fahmi, Roghan Asfaidar |
| 6. | Hamdard Manjan | Hamdard (Wakf) Laboratories Hamdard Marg, Delhi-110 006 | Ilaichi (*Electtaria cardamomum*) kalan, Amla (*Emblica officinalis*) dry, Post halaila zard (*Terminalia chebula*), Banslochan (*Bambusa bambos*), Zanjbeel (*Zingiber officinale*), Sangjarahat, Filfil siyah (*Piper nigrum*), Kabab khandan, Khoolanjan (*Alpinia galanga*), Namak Sambhar, Mileh firangi, Sat paudina (*Mentha spp*) |
| 7. | MDH Dant powder | Super Delicocies Pvt. Ltd. | i) *Acacia nilotica* ii) *Embelia tsjenam-cottam* iii) *Areca catechu* iv) *Juglans regia* v) *Curcuma amada* vii) *Syzygium aromaticum* viii) *Alpinia galanga* *Ficus elastica, Piper nigrum* Menthol, Eucalyptus oil. |
| 8. | Payakil | Gurukul Pharmacy Hardwar | *Acacia nilotica Suglans regia, Camphora officinatum, Azadirachta indica, Arcila vitrolutcum, Zanthoxylum armatum, Zanthoxylum armatum.* |

The above described formulations suffer from a number of disadvantages.
1. Some formulations have harmful components e.g. *Nicotiana tabacum* which ultimately spoil the teeth and gum.
2. Adulteration of plant material is often there. Therefore, the formulations have not been found very effective.
3. The product very often have cheap materials and expansive items are not used in the prescribed quantity. Therefore, the final product is not very useful.
4. Very often the amount of base material is more compared to active components and thus the product is not very useful.

OBJECTS OF THE INVENTION

The main object of the present invention is to provide a formulation useful as natural herbal tooth powder which obviates the drawbacks of the earlier tooth powders.

Another object is to provide a good tooth powder which can give effective protection to teeth and free them from any toxicity or toxic residue and irritation when regularly used. It should be cosmetically acceptable having pleasant odour and should not leave stain on teeth or fingers after use. Brightening the teeth by removing stains would be a prerequisite of the formulation.

Still another object of the present invention is to provide a formulation which contains natural aromatic and medicinal herbs useful for gums and teeth, which are safe, biodegradable and have very low mammalian toxicity.

SUMMARY OF THE INVENTION

The invention relates to a novel synergistic herbal composition useful as tooth powder and comprising the powders of Zanthoxylum sp, *Zingiber officinale*, sandalwood, roasted alum, common salt, Spilanthes sp., Pistacia sp., Quercus sp., Usnea sp., in the proportion 20–25%, 25–30%, 8.25–8.5%, 8–9%, 15–16.5%, 2–2.5%, 2–2.5%, respectively. As the ingredients are derived from herbal source, it is safe ecofriendly and does not produce harmful results. It is useful for treatment of swollen gums, yellow/staining of teeth, foul odour of mouth and sensitivity to hot and cold water and toothache.

DETAILED DESCRIPTION OF THE INVENTION

The present invention relates to a formulation of herbal tooth powder for teeth and gums. Since the components in the formulation are from herbal source it is very safe and ecofriendly and do not produce any adverse effect on the gums and teeth. It comprises of powders of *Zanthoxylum armatum* which is useful for toothache, powder of *Zingiber officinale* which is antiseptic due to presence of essential oil and resin, powder *Spilanthes calva*, whose flowers are chewed in toothache, resinous exudate of *Pistacia lentiscus* which has pleasant smell due to essential oil content and used as a filling for carious teeth. It is also used for cleansing the teeth and to remove bad odour of the mouth. Powder of gall nuts of *Quercus infectoria* plant has been used for its astringent effect. It is also useful for foul odour of mouth, toothache and swollen gums. *Usnea longissima* powder was used to make the powder soft and to improve the odour as it is rich in volatile oil and usnic acid.

The main object of the present invention is to provide a formulation useful as natural herbal tooth powder which obviates the drawbacks of the earlier tooth powders. Another object is to provide a good tooth powder which can give effective protection to teeth and free them from any toxicity or toxic residue and irritation when regularly used. It should be cosmetically acceptable having pleasant odour and should not leave stain on teeth or fingers after use. Brightening the teeth by removing stains would be a prerequisite of the formulation. The formulation which contains natural aromatic and medicinal herbs useful for gums and teeth, which are safe, biodegradable and have very low mammalian toxicity.

Since the components in the formulation are from herbal source, it is very safe and ecofriendly and does not produce any adverse effect. The formulation of present invention consist of (a) Powder of Zanthoxylum fruits that contain essential oil with disinfectant and antiseptic properties (Farooqi et al. J, Med. Arom Pl Sci., 20:441–450, 1998), (b) resinous exudate of *Pistacia lentiscus* a filler for carious teeth with teeth cleansing properties and able to remove foul odour of the moutn (Sushil Kumar et al. Medicinal Plants in Skin Care, CIMAP, 76–89, 1994), (c) powder of dried ginger (Zingiber officinale) with anti-inflammatory and antibacterial properties (Chopra et al., Glossary of Indian Medicinal Plants, 1956), (d) powder of Spilanthes calva which stimulates secretion of saliva (Farooqi et al., J. Med. Arom. Pl. Sci., 20:441–450, 1998), (e) powder of gall nuts of *Quercus infectoria* plant with astringent effect and able to check foul odour of mouth, toothache and swollen gums (The Wealth of India—Raw Materials, 1994), (f) powder of *Usnea longissima, Santalum albim,* plants (The Wealth of India— Raw Material, 1994), alum and common salt. A combination of medicinal plants powder with alum and common salt can be used as a good house hold tooth powder which results in the protection of teeth from different diseases.

The main diseases of the teeth include plaque, caries and pyorrhoea. Proper dental care is necessary for eliminating tooth decay and periodental diseases. The people living in Indian subcontinent largely depend on the traditional systems for the treatment of toothache, caries and other diseases related to teeth. The traditional herbal preparations for dental care comprise of various types of herbal powders and chewing sticks made out of young woody stems or root pieces.

The natural herbal products are in demand for use to control dental diseases. The natural herbs are harmless. as they don't have side effects. They also have low mammalian toxicity and can be handled safely.

The plants used in this formulation are very useful in controlling pyorrhoea, tooth hypersensitivity, and are reported to be useful for relieving gum inflammation and tooth ache (Farooqi et al. J. Med. Arom. Pl. Sci. 20:441450, 1998). *Zanthoxylum armatum* plant as called toothache fruit as its main use is in toothache. Fruits of *Z. armatum* contain essential oil (1.5%). The main constituent of oil is linalool. The oil is disinfectant and antiseptic; therefore, fruit powder is used for toothache. Therefore, *Z. armatum* fruits are used as a component in the preparation of this formulation.

*Pistacia lentiscus,* resinous exudate was also used in the preparation of dental powder. The resin has pleasant smell due to the presence of essential oil (12%) and is used as a filler for carious teeth, for cleansing of teeth and to remove foul odour of the mouth. Powder of dried ginger (*Zingiber officinale*) was used as it contains resin and essential oil and it has anti-inflammatory and antibacterial properties (Sushil Kumar et al., Medicinal Plants in Skin Care, CIMAP, 76–89, 1994). In the present formulation, the powder of Spilanthes calva was also used as it has property of stimulating secretion of saliva (Farooqi et al, J. Med. Arom. Pl. Sci., 20:441–450, 1998). Paste of its flower is used in toothache or flower as such is chewed in toothache. Powder of gallnuts of Quercus inflectoria plant was used due to its astrinent properties (The Wealth of India—Raw Materials, 1994). The powder is rich in tannic acid (50–70%). It is very useful for foul odour of mouth, toothache and swollen gums. Powder of *Usnea longissima* was used as it contains usnic acid and volatile oil and considered useful for gums in traditional system of medicine. It is filamentous, pendulus lichen common in temperate and alpine Himalayas (The Wealth of India—Raw Materials, 1994). Santalum album powder was used as it is used for local inflammation in traditional systems of medicine. The powder is rich in essential oil (1.5–6%) (Chopra et al., Glossary of Indian Medicinal Plants, 1956).

The herbal powder is useful for bleeding and swollen gums, yellowing/staining of teeth, foul odour of mouth, toothache as well as for sensitivity to cold/hot water/food. The composition of the formulation is new, very safe, ecofriendly and does not produce any harmful effects. The herbal components used in this formulation have not been used in other dental powders so far.

The components in the formulation are from herbal source and are very safe and ecofriendly and therefore do not produce any adverse effect on the gums and teeth. It comprises of powders of *Zanthoxylum armatum* which is useful for toothache, powder of *Zingiber officinale* which is antiseptic due to presence of essential oil and resin, powder of *Spilanthes calva,* whose flowers are chewed in toothache, resinous exudate of *Pistacia lentiscus* which has pleasant smell due to essential oil content and used as a filling for carious teeth. It is also used for cleansing the teeth and to remove bad odour of the mouth. Powder of gall nuts of *Quercus infectoria* plant has been used for its astringent effect. It is also useful for foul odour of mouth, toothache and swollen gums. *Usnea longissima* powder was used to make the powder soft and to improve the odour as it is rich in volatile oil and usnic acid.

Accordingly, the present invention provides a formulation useful as natural dental powder or paste, which comprises of *Zanthoxylum armatum, Zingiber officinale* sandalwood, roasted alum, common salt, Spilanthes spp. Pistacia spp., Quercus spp., and Usnea spp. as 20–25%, 25–30%, 8.25–8.5%, 8–9%, 15–16.5%, 20–25%, 8.0–8.5% and 1–4% respectively.

In an embodiment of the invention, *Zanthoxylum armatum* powder used may be procured from flowers, fruits and leaves of the plant. In another embodiment *Zingiber officinale* powder used may be such as from rhizome, leaves and stem. Another embodiment sandalwood powder used may be such as from hardwood or soft wood. Another embodiment *Spilanthes calva* used from flower or plants and stimulates secretion of saliva. Another embodiment is *Qurecus infecteria* gallnut powder procured from gallnut of plant.

The composition is not merely a mixture of the constituents. It is new and the ingredients have synergistic effect.

Examples 1–4 illustrates as to how formulation has been developed and forms the basis for the development of herbal tooth powder.

EXAMPLE-1

Powder of Zanthoxylum flowers, turmeric, ginger (dried), salt and alum (after roasting) were mixed in the following proportion:

| | |
|---|---|
| Zanthoxylum_powder | 20 g |
| Ginger powder | 20 g |
| Turmeric powder | 50 g |
| Salt | 10 g |
| Alum (roasted) | 10 g |

The formulation was distributed for testing on a limited scale. It was not found very effective.

EXAMPLE-2

Another sample was prepared and this time following composition was used.

| | |
|---|---|
| Ginger dried | 25 g |
| Alum powder (roasted) | 10 g |
| Zanthoxylum_powder | 20 g |
| Usnea_powder | 20 g |
| Turmeric powder | 50 g |
| Salt | 20 g |

The formulation was leaving stain on fingers.

EXAMPLE-3

Essential oil of different plants was used along with *Pistacia lentiscus*. Some components of Example-2 were omitted.

| | | weight % |
|---|---|---|
| Dried ginger powder | 20 g | 28.6 |
| Zanthoxylum powder | 17 g | 24.3 |
| *Spilanthes calva* | 2.5 g | 3.57 |
| *Pistacia lentiscus* | 2.0 g | 2.85 |
| Turmeric | 5.0 g | 7.1 |
| Usnea powder | 6.5 g | 9.3 |
| Alum powder | 6.8 g | 9.7 |
| Salt | 5.0 g | 7.5 |
| Tulsi oi | 150 drops | |
| Eucalyptus oil | 50 drops | |
| Clove oil | 50 drops | |

The formulation was effective to some extent.

EXAMPLE-4

Sandal wood powder and fruits of *Quercus infectoria* were added and essential oils and turmeric were omitted.

| | | weight % |
|---|---|---|
| Zanthoxylum powder | 90 g | 26.5 |
| Ginger (dried) | 60 g | 17.6 |
| Usnea_spp. Powder | 45 g | 13.2 |
| Alum roasted | 30 g | 8.8 |
| Sandal wood powder | 45 g | 13.2 |
| *Spilanthes calva* | 15 g | 4.4 |
| *Pistacia lentiscus* | 15 g | 4.4 |
| *Quercus infectoria* | 20 g | 5.8 |
| Common salt | 20 g | 5.8 |

The product was given to different persons. The effect of Spilanthes on the tongue was more pronounced. So its quantity was decreased in the final formulation.

The invention is illustrated with the help of following examples and should not construed to limit the scope of invention.

EXAMPLE-5

| | | weight % |
|---|---|---|
| Zanthoxylum | 300 g | 25 |
| Ginger powder | 300 g | 25 |
| Sandal wood powder | 100 g | 8.25 |
| Alum roasted | 100 g | 8.25 |
| Common salt | 200 g | 16.50 |
| Spilanthes powder | 30 g | 2.50 |
| *Pistacia lenticis* | 30 g | 2.50 |
| *Quercus infectoria* | 100 g | 8.0 |
| Usnea powder | 50 g | 4.0 |

EXAMPLE-6

| | weight % |
|---|---|
| Zanthoxylum | 20 |
| Ginger powder | 30 |
| Sandal wood powder | 8.5 |
| Alum roasted | 80 |
| Common salt | 16.0 |
| Splanthes powder | 2.0 |
| *Pistacia lenticis* | 2.0 |
| *Quercus infectoria* | 8.5 |
| Usnea powder | 4.0 |

EXAMPLE-7

| | weight % |
|---|---|
| Zanthoxylum | 22 |
| Ginger powder | 28 |
| Sandal wood powder | 8.5 |
| Alum roasted | 9.0 |
| Common salt | 15.0 |
| Spilanthes powder | 2.0 |
| *Pistacia lenticis* | 2.0 |
| *Quercus infectoria* | 8.5 |
| Usnea powder | 4.0 |

Samples were given to 54 persons on a prescribed proforma during August 98 to December 98. Response was satisfactory.

Statistical Analysis of Survey

Project surveyed: Herbal tooth powder

Sample size: 54 human beings

Area covered: Lucknow—96% Outside Lucknow—4%

Methodology: Direct contact questionnaire method

Precisions:
1. Subjects were asked to return the filled questionnaire.
2. Questionnaire contained instructions for use.
3. The product was advised to be used with brush or finger either in the morning or night time.

Age group and sex of subjects: The group sampled ranged between 8–72 years with 63% male and 37% female (Table—1).

Effectiveness of:

Taste—78% reported that taste is good/acceptable and 29% reported that taste needs improvement to be more plesant to tongue (Table—2).

Odour—72% opined that odour was pleasant while 6% reported that odour needs improvement for better aroma (Table—3).

Texture—24% reported that texture is fine while 41% reported that it should be made more fine (Table—4).

Dental problems for which powder was used: 34% people used that product for bleeding gums, while 38% used it for swollen gums. About 33% persons tested the tooth powder for yellowing/staining of teeth while 26% used it for foul odour of mouth. 20% checked it for sensitivity to cold/hot water/food, 16% for toothache and 8% for loosening of teeth (Table—5).

Relief noticed: About 60% persons reported it moderately effective for bleeding gums, swollen gums, toothache, yellowing/staining of teeth and foul odour of mouth as well as sensitivity to cold/hot water/food.

Any adverse effect was not reported on teeth, tongue and in oral cavity. House hold grinder was used for powdering the ingredients.

The formulation is not a mere admixture resulting in mere aggregation of the properties of individual ingredients but a synergistic mixture resulting in enhanced effectiveness for tooth problems. In examples 5–7 the synergistic effect of the formulation of the present invention is detailed.

TABLE 1

Age distribution

| Age | Male | Female | Total |
|---|---|---|---|
| Less that 20 | 2 | 3 | 5 |
| 20–40 | 16 | 13 | 29 |
| Above 40 | 16 | 4 | 20 |
| Total | 34 | 20 | 54 |

TABLE 2

Taste

| Taste of the product | No. of users | Percentage |
|---|---|---|
| Acceptable | 42 | 78 |
| To be improved | 12 | 22 |

TABLE 3

Odour

| Odour of the Product | No. of users | Percentage |
|---|---|---|
| Acceptable | 39 | 72 |
| To be improved | 3 | 6 |
| Not commented | 12 | 22 |

TABLE 4

Texture

| Texture of the product | No. of users | Percentage |
|---|---|---|
| Fine | 13 | 24 |
| Can be made more powdered | 22 | 41 |
| Not commented | 19 | 35 |

TABLE 5

Problems and effectivity

| Problems* | Persons used (%) | Highly effective (%) | Moderately effective (%) | Low/slow effective | No action (%) | Total (%) |
|---|---|---|---|---|---|---|
| 1. Bleeding gums | 34 | 18 | 60 | 22 | — | 100 |
| 2. Swollen gums | 38 | 26 | 68 | 6 | — | 100 |
| 3. Toothache | 16 | 25 | 62 | 13 | — | 100 |
| 4. Yellowing/staining of teeth | 33 | 6 | 70 | 24 | — | 100 |
| 5. Loosening of teeth | 8 | — | 75 | — | 25 | 100 |
| 6. Foul odour of mouth | 26 | 25 | 75 | — | — | 100 |
| 7. Sensitivity to cold hot water/Food | 20 | 11 | 78 | — | 11 | 100 |

*Includes multiple uses by individual respondants

Advantage

1. The product composition is safe to be used orally as the components used in the formulation are of herbal origin and do not produce and adverse effect on the gums and teeth.
2. The product is ecofriendly and economically viable.
3. No harmful components like *N. tabacuni* is used which ultimately spoils the teeth and gums.

What is claimed is:

1. A synergistic composition comprising the pastes or powders of Zanthoxylum sp., *Zingiber officinale*, Sandalwood, Roasted alum, Common salt, Spilanthes sp., Pistacia sp., Quercus sp., Usnea sp. in the proportion of 20–25%, 25–30%, 8.25–8.5%, 8–9%, 15–16%, 2–2.5%, 2–2.5%, 8–8.5%, and 1–4% respectively.

2. A composition as claimed in claim 1, wherein the powder of *Zanthoxylum armatum* is obtained from its flowers, leaves, roots or fruits.

3. A composition as claimed in claim 1, wherein the ginger powder is extracted from the rhizome, stem or leaves of *Zingiber officinale*.

4. A composition as claimed in claim 1, wherein the Sandlewood powder used is obtained from Sandalwood hard wood or soft wood.

5. A composition as claimed in claim 1, wherein the paste or powder of *Spilanthes calva* is obtained from the flowers or plants.

6. A composition as claimed in claim 1, wherein the powder of *Quercus infectoria* is obtained from the gallnuts.

7. A formulation as claimed in claim 1, wherein the Usnea powder is obtained from *Usena longisima* lichens.

8. A composition as claimed in claim 1, wherein the resinous exudate *Pistacia lentiscus* is used.

* * * * *